United States Patent
Sonntag et al.

(10) Patent No.: US 8,535,935 B2
(45) Date of Patent: Sep. 17, 2013

(54) CELL CULTURE MEASURING SYSTEM AND METHOD FOR COMPARATIVE INVESTIGATIONS ON CELL CULTURES

(75) Inventors: Frank Sonntag, Chemnitz (DE);
Florian Mehringer, Konradsreuth (DE);
Niels Schilling, Mittweida (DE); Martin Jaeger, Dresden (DE)

(73) Assignee: Fraunhofer-Gesellschaft zur Foerderung der Angewandten Forschung E.V., Munich (DE)

( * ) Notice: Subject to any disclaimer, the term of this patent is extended or adjusted under 35 U.S.C. 154(b) by 458 days.

(21) Appl. No.: 12/733,112

(22) PCT Filed: Aug. 8, 2008

(86) PCT No.: PCT/DE2008/001348
§ 371 (c)(1),
(2), (4) Date: Jun. 1, 2010

(87) PCT Pub. No.: WO2009/021501
PCT Pub. Date: Feb. 19, 2009

(65) Prior Publication Data
US 2010/0261222 A1    Oct. 14, 2010

(30) Foreign Application Priority Data
Aug. 10, 2007    (DE) .......................... 10 2007 038 777

(51) Int. Cl.
*C12M 1/34*    (2006.01)

(52) U.S. Cl.
USPC ........................................ 435/287.1; 435/29

(58) Field of Classification Search
USPC .................................. 435/29, 287.2; 204/603
See application file for complete search history.

(56) References Cited

U.S. PATENT DOCUMENTS

| | | | |
|---|---|---|---|
| 3,370,175 A | 2/1968 | Jordon et al. | |
| 6,200,814 B1 | 3/2001 | Malmqvist et al. | 436/52 |
| 2006/0154361 A1* | 7/2006 | Wikswo et al. | 435/289.1 |
| 2008/0014575 A1 | 1/2008 | Nelson | 435/5 |
| 2008/0199974 A1 | 8/2008 | Frey et al. | 438/1 |

FOREIGN PATENT DOCUMENTS

| | | |
|---|---|---|
| DE | 19709649 | 9/1998 |
| DE | 19720997 | * 11/1998 |
| DE | 19720997 A1 | * 11/1998 |
| DE | 19920811 | 11/2000 |
| WO | WO 90/04645 A1 | * 5/1990 |
| WO | 03082469 | 10/2003 |

OTHER PUBLICATIONS

Machine Translation of DE19720997A1 (translated on Jul. 23, 2012).*

* cited by examiner

*Primary Examiner* — Michael Hobbs
(74) *Attorney, Agent, or Firm* — Jacobson Holman PLLC

(57) ABSTRACT

A cell culture measuring system and to a method for comparative investigations on cell cultures. In a cell culture measuring system, cell cultures are cultivated on a cell culture carrier within a flow passage. An inflow and an outflow for a liquid culture medium and at least two sensors are present. At least one further inflow for a test liquid is arranged in the flow direction of the culture medium between the inflow for the culture medium and the outflow of the flow passage so that the test liquid flowing through the flow passage by displacement of the culture medium only flows around and/or over some of the cells present on the cell culture carrier. At least one sensor is arranged in the region of the cells not influenced by test liquid and at least one sensor is arranged in the region of cells influenced by test liquid.

16 Claims, 2 Drawing Sheets

CELL CULTURE MEASURING SYSTEM AND METHOD FOR COMPARATIVE INVESTIGATIONS ON CELL CULTURES

This is a national stage of PCT/DE08/001348 filed Aug. 8, 2008 and published in German, which has a priority of German no. 10 2007 038 777.8 filed Aug. 10, 2007, hereby incorporated by reference.

FIELD OF THE INVENTION

The invention relates to a cell culture measuring system and to a method for comparative investigations on cell cultures. It can in particular be used when functional effects on living cultivated cells as a consequence of media which can influence the cells should be carried out and evaluated. In this respect, the behavior or the change of the morphology of cells under the influence of substances contained in test liquid or of test liquids which cause such effects can be detected.

BACKGROUND OF THE INVENTION

In this respect, it is usually desired that comparative investigations are carried out on living cell cultures to be able to make corresponding statements on the effects of cell-influencing media. It is accordingly necessary that the cell cultures influenced in different manners are otherwise cultivated under the same conditions so that different influences acting on cell cultures can be precluded.

A method and an apparatus are thus known from EP 0 394 406 B1 for the detection of an effect of a cell-influencing medium on living cells in which a microflow chamber in which living cells are cultivated is flowed through by solutions or suspensions which contain a cell-influencing medium. In this respect, however, all the living cells contained in the microflow chamber are influenced by the cell-influencing medium so that, for a comparative investigation, at least one second microflow chamber must always be present in which an investigation can take place without the influence of a cell-influencing medium. It is, however, problematic by the use of two such mutually separate microflow chambers to be able to maintain the desired same conditions for the cell investigations. There is moreover no possibility in this known technical solution to carry out an investigation with respect to interactions on cells caused by cell-influencing media and also to carry out the recognition of a forwarding of a stimulus from cells influenced by the cell-influencing medium to cells not influenced by these media.

The last-named aspect is, however, also problematic in the apparatus for the carrying out of investigations on cell cultures described in DE 199 20 811 B4. In this known apparatus, a trough-shaped receptacle should be used in which a cell culture in a liquid culture medium is contained at the base side. A part space can be separated off the remaining part as a reaction space by a separator which is inserted into the receptacle and which can be introduced down to the base of the receptacle. In such a reaction space, cell-influencing media can then act on the cells arranged there, whereas another region of the receptacle cannot be influenced by such media.

On the introduction of such a separator which can be formed in the manner of a ram, leaks can, however, occur so that a cell-influencing medium can be discharged from the reaction space and can enter into the other part of the receptacle.

If, however, a separator is introduced so that a complete closure of a reaction space occurs, the forwarding of information and/or stimuli within a cell culture completely contained in a receptacle cannot be investigated. This situation in particular affects the forwarding of information and/or stimuli between cells influenced by a medium to cells not influenced by the medium.

SUMMARY OF THE INVENTION

It is therefore the object of the invention to propose possibilities with which comparative investigations on cell cultures can be carried out under the same conditions on cells which are influenced by a test liquid and cells which are not influenced by a test liquid.

A cell culture measuring system in accordance with the invention is formed in this respect so that a cell culture carrier having cell cultures cultivated thereon is arranged within a flow passage at which at least one inflow and at least one outflow for a liquid culture medium are present. A liquid culture medium is conducted through the flow passage from the inflow to the outflow. At least one further inflow for a test liquid is present at the flow passage. This inflow is arranged in the flow direction of the culture medium between the inflow for the culture medium and the outflow of the flow passage so that it displaces the culture medium, and thus the test liquid flowing through the flow passage only flows around and/or over a part of the cells present on the cell culture carrier. At least two sensors are arranged in the region of the cell culture, with at least one sensor being arranged in the region of cells not influenced by test liquid and with a least one further sensor being arranged in the region of cells influenced by test liquid.

Cell functions or effects of the cell metabolism as well as changes in the morphology of cells can be detected using these sensors.

A test liquid thus enters into a flow passage and the displacement of the culture medium flowing through the flow passage takes place while observing specific flow conditions so that a relatively sharp boundary surface forms between the culture medium and the test liquid on the throughflow of both liquids and in this respect practically no convection or diffusion of test liquid or of media contained in a test liquid and influencing the cells takes place outside the region which should be used for the investigation of the influence of a test liquid.

This can be achieved, for example, by a suitable control or regulation of the volume flows of culture medium and/or test liquid flowing through the flow passage. It can be sufficient to conduct culture medium through the flow passage via the inflow and the outflow at a constantly maintained volume flow and only to influence the volume flow of the test liquid corresponding directly which is introduced into the flow passage via the further inflow.

A test liquid per se can already cause a cell-influencing effect. However, such media can also be contained in a test liquid in dissolved form or can be a test liquid or a suspension.

To ensure that only liquid is conducted through the flow passage which does not contain any gas bubbles, a semipermeable membrane or a micro-screen, as examples for bubble traps, can be arranged at one or more inflows via which a liquid culture medium and/or a test liquid can flow into the flow passage. Suitable micrometering systems known per se can be used for the influencing of the supplied volume flows of culture medium and/or test liquid.

The sensors which are used in the comparative investigations and which are arranged in the region of the cells not influenced by test liquid and in the region of test cells influenced by test liquid should be the same sensors in each case which are sensitive in the same manner. A plurality of the same sensors, e.g. pairs or triples, having different sensitivity can, however, also be arranged in non-influenced or influenced regions of the cell culture. Different comparative investigations can then thereby be carried out on cells simultaneously.

It is in particular advantageous in investigations in which a forwarding of information and/or stimuli between cells should be carried out to arrange the sensors at respectively the same intervals from one another. This then also relates to additional sensors which are then arranged in a region not influenced by test liquid and in this respect at least two such sensors then have different spacings from cells which have been influenced by test liquid.

As already addressed, at least one inflow of test liquid should be arranged between an inflow for culture medium and the at least one outflow at a flow passage. This at least one further inflow for test liquid should then open into the flow passage at an angle between 0° and 90°, preferably 45° and 90°, with respect to the flow direction of the culture medium, with this applying at least to that region of the flow passage in which liquid culture medium and test liquid then flow together out of the flow passage in the direction of an outflow.

There is also advantageously the possibility in the invention to form sensors directly at or also in the cell culture carrier, which promotes the possibility of a modular structure of a cell culture measuring system.

A cell culture carrier which can be used in a cell culture measuring system in accordance with the invention can be formed from polymer material. This polymer material can be functionalized selectively regionally at its surface before the actual use in order to be able to selectively achieve or suppress an adhesion of cells. Such a functionalizing can be achieved by irradiation with electromagnetic radiation in the wavelength range of ultraviolet light under the simultaneous influence of a reactive gas.

Such a cell culture carrier, but also other parts of a cell culture measuring system in accordance with the invention such as also a cover element, can be formed from an optically transparent polymer material. The possibility is thereby additionally opened up of being able to carry out microscopic investigations at the cell culture.

It is moreover favorable with the cell culture measuring system in accordance with the invention to design the flow passage geometrically such that a larger width is present in the region of an inflow for test liquid than applies to the region at which an inflow for culture medium is arranged. The flow speed of the liquid culture medium in the region of the inflow for test liquid is thereby reduced and a predominantly laminar flow is formed in this region which can be utilized considerably better with a sharp boundary layer for the formation of a region in which cells are influenced by test liquid by displacement of liquid culture medium by test liquid. A laminar flow of test liquid and culture medium should be observed.

With a cell culture measuring system in accordance with the invention, as already addressed, different sensors can be used, with this applying to sensors which are respectively the same, but also to sensors having different sensitivity which can be arranged in the regions influenced by test liquid and in the regions not influenced by test liquid. Such sensors can be pH sensitive, oxygen sensitive, glucose sensitive, optically sensitive (morphology, fluorescence), electrically sensitive (electrical potentials) and/or electro physiologically sensitive (concentrations).

In the comparative investigations of cells, a determination should be carried out by the sensors with time resolution in order in particular to enable the possibility of the determination of a mass transfer and of a forwarding of information and/or stimulus. Measurement signals can thus be detected at specific times, for example when the inflow for test liquid has been opened. An influence is then exerted on a region of cells by the test liquid. The time can then be detected up to which an effect of test liquid on cells occurs and subsequently then this effect in turn has an influence on cells which are arranged in a region which remains uninfluenced by test liquid.

The respective measured values detected in time can then be subsequently evaluated and the respective effect of the test liquid can be determined.

A plurality of inflows can also be present, arranged after one another at the flow passage, at a cell culture measuring system in accordance with the invention in the direction of flow of the liquid culture medium. Different concentrations of a medium influencing the cells can thereby be achieved in different regions of the flow passage so that a differentiated influencing of cells with test liquid and/or with a medium influencing the cells can be achieved in a differentiated manner. Different test liquids which contain different media influencing cells can, however, also be supplied alone or additionally in this form. Cells can thus be investigated under the same conditions except for the respective different composition of test liquids.

The one inflow or also the plurality of inflows can be switched off or also switched on/opened in a defined manner. Test liquid can thus, for example, be supplied over a presettable time period and the supply of test liquid can then be ended again. The extent can, for example, be investigated in this manner to which the effect of the medium influencing the cells drops off again or is partly or completely irreversible.

In the invention, the conditions in the cell cultivation and in the investigation of the medium influencing cells can easily be kept constant and in this respect comparative investigations can be carried out on cells with a medium influencing the cells and simultaneously, under the same conditions, also on cells which are not influenced by such a medium. The uninfluenced cells represent a reference for the comparative investigations.

A cell culture measuring system in accordance with the invention can, however, also have a closed flow passage. That region which also influences the respective cells by a cell-influencing medium can also be influenced very directly in its size and with the corresponding number of cells by a direct influencing of the volume flows of liquid culture medium and test liquid conducted through the flow passage.

A procedure can be followed in the carrying out of the investigations such that first cells are cultivated on a cell culture carrier, which can also take place in the cell culture measuring system in accordance with the invention, and in this respect also already in the flow channel. In this respect, a culture medium without test liquid can also flow around and/or over all cells. Subsequently, at least one test liquid having a known composition can then be supplied for a presettable time period so that only some of the cells are flowed around and/or over by test liquid. After ending the supply of test liquid, only culture medium can then again be supplied to all cells. In this respect, a detection can take place with all sensors during the whole time. Measured signals can naturally in this respect be detected continuously or also intermittently at presettable time intervals.

BRIEF DESCRIPTION OF THE DRAWINGS

The invention will be explained in more detail by way of example in the following.

There are shown

DETAILED DESCRIPTION OF THE PREFERRED EMBODIMENTS

Figure 1:
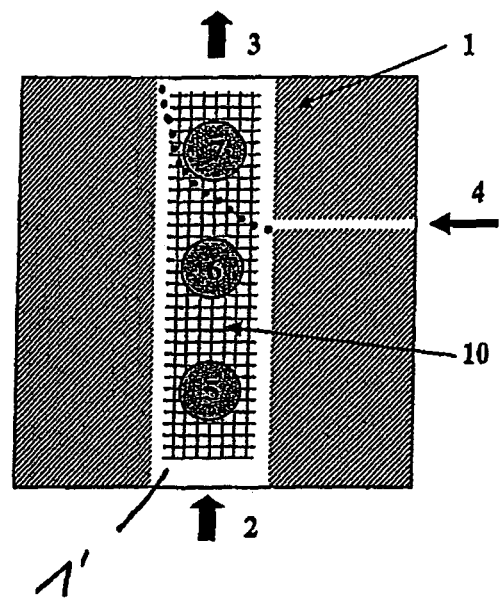
FIG. 1 in schematic form, a plan view of an example of a cell culture measuring system in accordance with the invention.

In the example of a cell culture measuring system 1 in accordance with the invention shown in FIG. 1, a flow passage 1' is present which has an inflow 2 for a liquid culture medium and starting from which the liquid culture medium flows through the flow passage 1' in the direction toward an outflow 3 of the flow passage 1'. It becomes clear from FIG. 1 that the flow passage 1' has a widened regions/cross-section between the inflow 2 and the outflow 3. A cell culture carrier 10 is arranged there on which cell cultures are arranged/formed.

Sensors 5, 6 and 7 are present on the cell culture carrier 10 with which cell functions can be detected.

The sensors 5, 6 and 7 are arranged at equal intervals from one another and in this example on a diagonal axis of the cell culture carrier 10 formed in square shape here.

A further inflow 4 for a test fluid is present at a side of the flow passage 1' through which inflow test liquid can flow in a defined form into the flow passage 1'. The inflow 4 is here aligned at an angle of 90° between the inflow 2 and the outflow 3 with respect to the flow direction of the culture medium.

It is moreover illustrated by FIG. 1 how the test liquid flowing in through the inflow 4 displaces culture medium and a region with cultivated cells on the cell culture carrier 10 is influenced by the test liquid or by a medium contained in a test liquid and influencing the cells. In this example, it is the right hand upper corner in the illustration of FIG. 1 in which the sensor 7 is arranged with which a detection of cells influenced by test liquid is possible. The same detection can be carried out on cells not influenced by test liquid using the sensors 5 and 6 which are arranged in regions which remain uninfluenced by test liquid.

Figure 2:
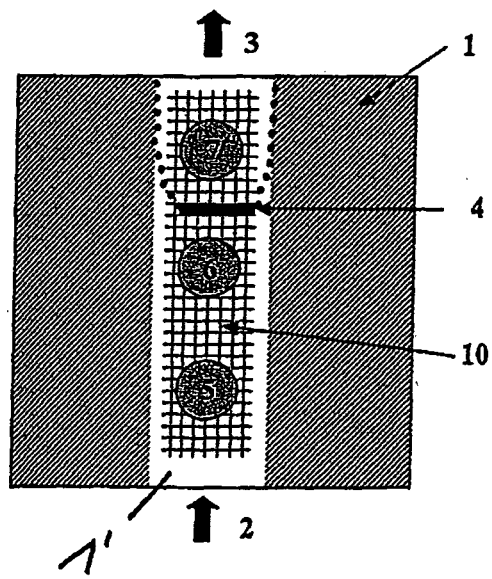
FIG. 2 in schematic form, a further example in plan view of a cell culture measuring system in accordance with the invention.

The example shown in FIG. 2 only differs from the example in accordance with FIG. 1 by the formation of the inflow 4 for test liquid. It is not conducted through the wall of the flow passage 1' laterally from the outside, but rather the inflow 4 for test liquid in this example is admittedly formed at the same side and also in the center of the cell culture carrier 10, but on the cell culture carrier 10.

Figure 3:
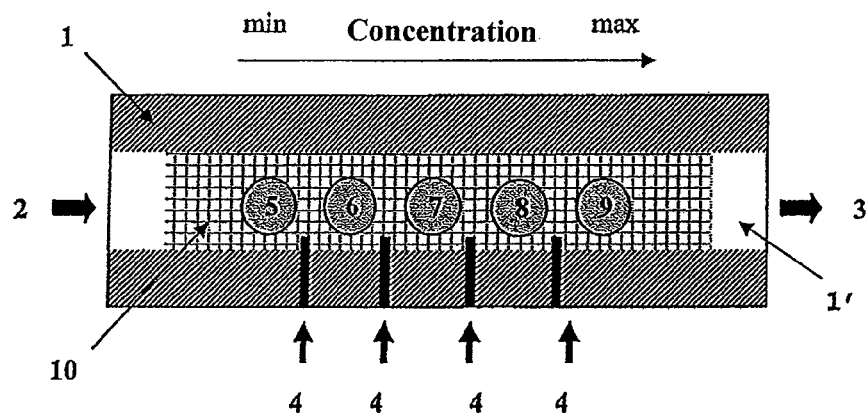
FIG. 3 in schematic form, a plan view of an example of a cell culture measuring system in accordance with the invention having a plurality of inflows for test liquid.

In the example shown in FIG. 3, a plurality of inflows 4 for test liquid are present at a side of the flow passage 1' and are here arranged equidistantly from one another.

A direct influencing of a concentration of test liquid or of a medium which influences the cells and is contained in the test liquid can thereby be changed in a locally differentiated manner, as is illustrated by the arrow shown above. Accordingly, cells which are arranged further in the direction of the outflow 3 after inflows 4 for test liquid are acted on by an increased concentration. The influence on the cells dependent on the concentration can also be detected by arrangement of a plurality of sensors 7 in this region.

Figure 4:
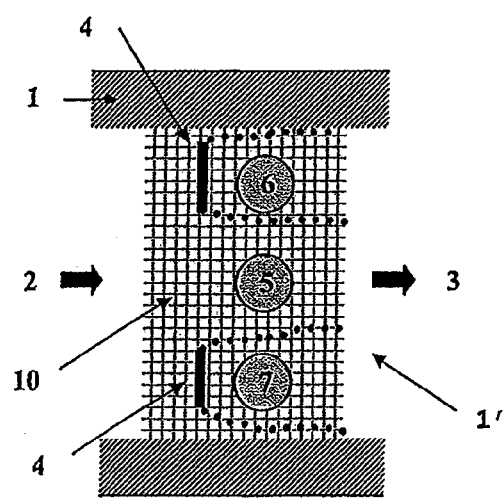
FIG. 4 an example of a cell culture measuring system in accordance with the invention in a plan view having two outflows and one inflow for a culture medium.

In the example shown in FIG. 4 of a cell culture measuring system in accordance with the invention, an inflow 2 is present at the center at a flow passage 1'. The supplied liquid culture medium then flows in the direction of the outflow 3.

In this example, two inflows 4 for test liquid are moreover arranged in the flow passage 1' so that cells and sensors 6 and 7 are flowed around and/or over by test liquid, whereas a region of cells not influenced by test liquid and the sensor 5 remain. Investigations can thus be carried out on cells with a plurality of test liquids under the same conditions, that is, also with different media influencing cells.

Only culture medium is conducted through in the central region of the flow passage 1'.

The invention claimed is:

1. A cell culture measuring system for comparative investigations on cell cultures in which cell cultures are cultivated on a cell culture carrier, the cell cultures being arranged within a flow passage having at least two sensors and an inflow and an outflow for a liquid culture medium, said cell culture measuring system comprising at least one further inflow for a test liquid arranged at an entry point in a flow direction of the culture medium between the inflow and the outflow of the culture medium through the flow passage so that the test liquid flowing through the flow passage by displacement of the culture medium only flows around and/or over some of the cells present on the cell culture carrier and at least one sensor being arranged in a region of the cells in the flow passage upstream of the entry point not influenced by the test liquid and at least one further sensor arranged downstream of the entry point in a region of cells in the flow passage influenced by the test liquid.

2. The cell culture measuring system in accordance with claim 1, wherein volume flow of culture medium and/or test liquid conducted through the flow passage is controlled or regulated.

3. The cell culture measuring system in accordance with claim 1, wherein the test liquid is a medium influencing the cells or contains a medium influencing the cells.

4. The cell culture measuring system in accordance with claim 1, wherein at least one inflow for test liquid opens into the flow passage at an angle between 0° and 90° with respect to the flow direction of the culture medium.

5. The cell culture measuring system in accordance with claim 1, wherein the at least two sensors are formed directly at or in the cell culture carrier.

6. The cell culture measuring system in accordance with claim 1, wherein at least one cell culture carrier is formed from a polymer material and is selectively regionally functionalized at its surface.

7. The cell culture measuring system in accordance with claim 1, wherein at least three of the sensors are arranged at equal intervals from one another.

8. The cell culture measuring system in accordance with claim 1, wherein pH sensitive, oxygen sensitive, glucose sensitive, optically sensitive, electrically sensitive and/or electrophysiologically sensitive sensors are present.

9. A cell culture measuring system for comparative investigations on cell cultures in which cell cultures are cultivated on a cell culture carrier, the cell cultures being arranged within a flow passage having at least two sensors arranged across the flow passage between an inflow and an outflow for a liquid culture medium, said cell culture measuring system comprising at least one further inflow for a test liquid arranged in a flow direction of the culture medium between the inflow and the outflow of the culture medium through the flow passage so that the test liquid flowing through the flow passage by displacement of the culture medium only flows around and/or over some of the cells present on the cell culture carrier and at least one sensor being arranged in a region of the cells in the flow passage out of a path of flow of the test liquid and at least one further sensor is arranged in a region of cells in the flow passage influenced by the test liquid.

10. The cell culture measuring system in accordance with claim 9, wherein volume flow of culture medium and/or test liquid conducted through the flow passage is controlled or regulated.

11. The cell culture measuring system in accordance with claim 9, wherein the test liquid is a medium influencing the cells or contains a medium influencing the cells.

12. The cell culture measuring system in accordance with claim 9, wherein at least one inflow for test liquid opens into the flow passage at an angle between 0° and 90° with respect to the flow direction of the culture medium.

13. The cell culture measuring system in accordance with claim 9, wherein the at least two sensors are formed directly at or in the cell culture carrier.

14. The cell culture measuring system in accordance with claim 9, wherein at least one cell culture carrier is formed from a polymer material and is selectively regionally functionalized at its surface.

15. The cell culture measuring system in accordance with claim 9, wherein at least three of the sensors are arranged at equal intervals from one another.

16. The cell culture measuring system in accordance with claim 9, wherein pH sensitive, oxygen sensitive, glucose sensitive, optically sensitive, electrically sensitive and/or electrophysiologically sensitive sensors are present.

* * * * *